United States Patent [19]
Radd et al.

[11] 3,942,546
[45] Mar. 9, 1976

[54] CORROSION MONITORING AND COMPOSITION-ANALYTICAL APPARATUS

[75] Inventors: Frederick J. Radd; Donald H. Oertle, both of Ponca City, Okla.

[73] Assignee: Continental Oil Company, Ponca City, Okla.

[22] Filed: Sept. 11, 1973

[21] Appl. No.: 396,170

Related U.S. Application Data

[60] Division of Ser. No. 301,391, Oct. 27, 1972, which is a continuation of Ser. Nos. 88,112, Nov. 9, 1970, Ser. No. 858,243, Sept. 15, 1969, and Ser. No. 670,317, Sept. 25, 1967, abandoned.

[52] U.S. Cl. .......................... 137/93; 73/23; 417/49
[51] Int. Cl.² .................. G05D 11/13; G01N 31/04
[58] Field of Search .............. 137/93; 417/49; 73/23

[56] References Cited
UNITED STATES PATENTS

| | | |
|---|---|---|
| 2,671,336 | 3/1954 | Hulsberg .................................. 73/23 |
| 2,671,337 | 3/1954 | Hulsberg .................................. 73/23 |
| 2,787,903 | 4/1957 | Beard ....................................... 73/23 |
| 3,050,622 | 8/1962 | Boyer et al. ....................... 417/49 X |
| 3,409,211 | 11/1968 | Bachler ................................... 417/49 |
| 3,426,579 | 2/1969 | Lebel et al. .............................. 73/23 |
| 3,460,745 | 8/1969 | Lamont, Jr. ........................... 417/49 |

*Primary Examiner*—William R. Cline
*Attorney, Agent, or Firm*—Robert B. Coleman, Jr.

[57] ABSTRACT

A simple apparatus and process for monitoring a selected component of a fluid system are provided wherein the apparatus comprises a simple diffusion probe, an electronic pumping means and a reading means whereby the diffusion and pumping rate are read directly as electrical current.

5 Claims, 7 Drawing Figures

CORROSION MONITORING AND COMPOSITION-ANALYTICAL APPARATUS

This application is a division of application Ser. No. 301,391, filed Oct. 27, 1972 which is a continuation of a sequence of co-pending continuation applications entitled, "Corrosion Monitoring and Composition-Analytical Apparatus," Ser. No. 88,112 filed Nov. 9, 1970; Ser. No. 858,243 filed Sept. 15, 1969; and Ser. No. 670,317 filed Sept. 25, 1967, now abandoned.

This invention relates generally to detection of selected components in a fluid system and more particularly to the continuous instantaneous monitoring of a selected component as a free or a dissolved gas in a rapidly changing or rapidly moving fluid system such as a chemical reactor, a storage vessel or a pipeline. A preferred application monitors hydrogen in a storage vessel or pipeline wherein said hydrogen is present or produced in the fluid system as a function of corrosion or decomposition or pyrolysis in the system.

Numerous methods and types of equipment are available for detecting certain constituents of a composition, detecting leaks in vacuum systems, monitoring cumulative changes in a system, balancing electrolytic corrosion protection systems, electronically sampling or controlling fluid systems. These features all illustrated by U.S. Pat. Nos. 2,393,650; 2,526,038; 3,257,841; 3,278,837; 3,356,287; 3,426,529; 3,490,480; 3,498,900; and 3,528,282 and by "Unusual Pipeline Failures Traced to Hydrogen Blisters" on pages 99–101 in the Dec. 20, 1954 issue of the Oil and Gas Journal.

Even with these numerous systems there is a need for an apparatus and method for monitoring chemical reactions and concentrations which are subject to rapid change. A simple apparatus which can be readily moved and modified for plant and field use is needed. A system which has continuous and practically instantaneous response and which can be readily adapted to for a continuous control system would fill a long-felt need.

The process and apparatus of this invention overcomes many of the prior art problems and supplies many of the needed features for a continuous, instantaneous monitoring and control system of general applicability in chemical, petroleum and other fields of technology.

According to this invention there is provided an apparatus for continuous instantaneous monitoring a selected component in a fluid system comprising gas, liquid, gas and solid, liquid and solid, or a mixture thereof; said apparatus comprising a probe means connected to a pumping means, said probe means which can be inserted into said fluid system having a body portion and a diaphragm portion which will allow diffusion of said selected component defining a closed cavity which is evacuated and which connects to and communicates with said pumping means, said pumping means having an electrical molecule pumping means and a current indication means which electronically removes molecules from said cavity, maintains evacuation of said cavity and indicates the molecule pumping rate as electrical current.

This invention also provides a process for continuous instantaneous monitoring of a selected component in a fluid system comprising gas, liquid, gas and solid, liquid and solid or a mixture thereof comprising assembling a monitoring apparatus comprising a simple probe means and a pumping means, said probe means having a body portion and a diaphragm portion which will allow diffusion of said selected component defining a closed cavity which can be evacuated to a suitable low pressure, said cavity connected to and communicating with said pumping means, said probe means being suitable for insertion into said fluid system, inserting said probe into said fluid system, promoting diffusion of said selected component into said cavity by evacuating said cavity to a suitable low pressure, maintaining said cavity at a suitable low pressure using an electrical pumping means to electronically pump molecules of said selected component from said cavity, and reading said pumping rate as electrical current.

The simple monitoring apparatus of this invention can be readily modified to indicate, record or control a function of the fluid system with rapid response time on the order of minutes or seconds. Previous monitoring systems having comparable response times involve complex, fragile and expensive sampling and sensing means. Previous systems which were rugged enough for field or plant use were cumulative or had response times which were too long for analytical and process control purposes. The system of this invention provides a low response time system which is simple and practical for field and plant use.

Figure 1:
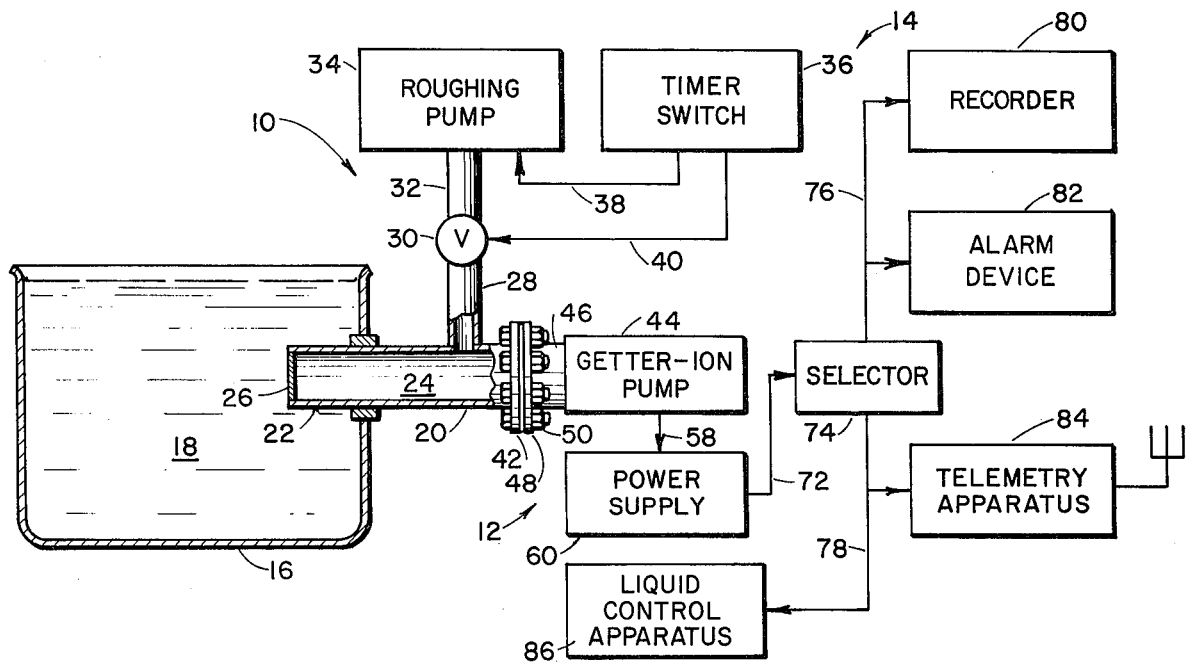
FIG. 1 is a block diagram of gas phase monitoring apparatus constructed in accordance with the invention.

A preferred embodiment of this invention comprises the simple monitoring system and a control system which can control corrective measures in response to the function being monitored. These corrective measures can be addition of inhibitor, initiator, reactant or diluent to a system; variation of the rate of flow of electrical, heat or other form energy in a system; or variation in the flow rate of a stream in a system. The control system can be a feedback system, a feed forward system or a combination using dual monitoring components for comparison and adjustment of the corrective measures. Conventional components can be used in the control system for each function and the system can be modified to perform particular complex functions which will be apparent to those skilled in the art in view of this disclosure.

Monitoring systems of this invention function by promoting diffusion of a selected component of the fluid system through the diaphragm portion of the probe into the probe cavity from which it diffuses into the electronic pumping and detection means. The selected component is in the form of atomic or nascent gas, ion or a simple molecule which can readily diffuse into or be generated in the probe cavity. These forms of the selected component will be referred to collectively herein as a free gas. The free gas can also comprise more than one type of atom or molecule for example hydrogen, oxygen and nitrogen. The exact composition of the free gas will depend upon the diffusion characteristics of the diaphragm portion of the probe and the constituents in the fluid system. Diffusion of the free gas into the probe cavity refers to actual physical passage of a free gas component through the probe diaphragm as well as generation by some electrochemical means of the free gas in the cavity without physical passage through the diaphragm, for example hydrogen diffusion and proton emission from the inner surface of the probe cavity. With more than one component in the free gas each component can be pumped from the cavity by a single pumping means, selective electronic gates or diffusion membranes which can be used with miltiple electronic pumping means or chemical gettering agents can be used to trap certain components. These methods using conventional high-vacuum electronic technology will be apparent to those skilled in the art from this disclosure.

The diffusion characteristics of the diaphragm portion of the probe and the selected component of the fluid system determine the composition of free gas in the probe cavity. Geometric design, size, thickness and material of construction determine the diffusion rate of the free gas. The diffusion rate should be in a range to give reasonably accurate pumping rate readings without overloading the pumping means and maintaining evacuation at a suitable low pressure of the cavity. Magnitude of the electrical current required for the ultimate use of the current must be considered in selecting the diffusion rate. A suitable low pressure is below about $1 \times 10^{-2}$ Torr, preferably in the range of about $1 \times 10^{-4}$ - $1 \times 10^{-50}$ Torr. At the preferred evacuation pressure range the diffusion rate varies little with pressure variation.

The probe can be of numerous geometric configurations. A preferred configuration is a generally cylindrical shape in which the diaphragm can be the entire probe, a cylindrical sleeve, a round end section or a combination of these. Another, preferred configuration of the probe utilizes a tubing shape which can be coiled and connected to the pumping means at two ends or the probe can be arranged in numerous complex or simple configurations. Likewise, the probe can have a rectangular cross-section configuration. The probe can also be fabricated into the wall of a vessel containing the fluid system to present only a flat surface to the fluid. The probe can also be fitted into or around a by-pass conduit having valves to isolate the probe for easy removal. Other configurations will be apparent to those skilled in the art in view of this disclosure.

An important feature of the probe of this invention is the material of construction. Just as the use of a high-vacuum system simplifies the probe construction by eliminating any requirement for low cavity volume, capillary passages or high surface area probes, selection of the material of the probe diaphragm portion can be used to give a practically instantaneous response which can be used directly. By using a probe material which is classified herein as active or catalytic rather than passive, the rate diffusion of the selected component will have a multiplied ratio relationship to the function that is being monitored.

For example, it has been found that certain types of steel actually react with a certain fluid medium to produce nascent hydrogen at the surface. Different types of steel have different rates of reaction for this phenomenon. Thus, for monitoring the corrosive nature of a certain fluid system or the passage of slugs or an interface of this system, a high reactivity probe material could be used which would give a fast response and a large output signal. This probe would be excellent for control of addition of corrosion inhibitor to a pipeline to stop actual corrosion, rather than adding more inhibitor than is necessary with a cumulative corrosive monitoring system. By using inhibitor only as needed and where it is needed expense and contamination of the fluid system are reduced.

For a chemical reaction system the use of a less active material such as a catalytic or passive probe material would be desired to prevent too rapid response and overcompensation by the control system. Active material is used herein to designate material which actually reacts with the fluid system to produce a free gas which is a function of the selected component being monitored. Catalytic material refers to a material which affects the promotion of a free gas but is not consumed by the reaction producing the free gas. Passive material does not affect formation of the free gas but permits diffusion of the free gas. Thus, a diaphragm material can be classified in more than one group for a multiple component fluid system. Ideally, the diaphragm configuration and material can be selected according to the fluid system being monitored to give the response characteristics desired and an output signal which can be used directly. However, for some applications amplification or modification of the signal may be necessary.

The active, catalytic or passive nature of the probe diaphragm material are illustrated by carbon steel, 3.5% nickel steel, 10% ferrous-palladium alloy (this is magnetic), nickel-plated carbon steel and palladium materials. For monitoring sour gas or sour crude corrosion in a pipeline a carbon steel material is an active material which would react with the sour crude to produce nascent hydrogen. This turns out to be an excellent application thereof. The reaction rate would be faster than that with the pipeline material to give a fast high sensitivity monitor probe. This probe could be used with a sour or acidic fluid system in an inert reactor such as a nickel stainless steel or glass-lined reactor where nascent hydrogen gas would not be present because it produces nascent hydrogen. In this application a passive palladium would not work in a liquid or two phase system where hydrogen is not present. There are non-metallic materials such as ceramics, crystalline materials, and polymers that have a combination action. For example a beryl crystal exhibits directional diffusion characteristics; for instance, helium can diffuse through the crystal along the c-axis. Probes having combination effects can also be made using several materials such as coated materials or laminates, for example nickel coated steel, coated polymeric material or impregnated polymeric material. Metallic material which can be used for a probe include aluminum, nickel, copper, titanium, lead, zinc, tin, antimony, cobalt, tungsten and iron. Noble metals such as gold, silver, platinum, palladium and ruthenium can be used for passive materials. There are numerous ferrous alloys which can be used for a probe including carbon steel, low carbon steel, stainless steel (such as nickel steel, chromium steel, and vanadium steel), silicon steel and cast iron. Crystalline materials which can be used include quartz, beryl, alumina, silica, and carbon. Ceramics and glass will also be included in the crystalline materials. Polymeric materials which can be used include ethylenic polymers such as ethylene, ethylene/propylene, and ethylene/propylene/diene polymers (generally designated as EPM polymers), rubber, (such as styrene/butadiene, natural, polybutadiene and polyisoprene), epoxy formulations, phenol-formaldehyde polymers, nylon, polyester polymers, vinylic polymers and vinyl halide polymers. Combinations of these materials can be used to make probes having certain diffusion properties. For example, laminates can be used that allow diffusion of several selected free gases, coated metals can be used to give catalytic activity at the probe surface with selective differsivity and semiconductor probe materials can be used so that the activity or diffusion characteristics can be controlled by an electrical bias current on the diaphragm. That is, free gas diffusion or catalytic activity can be turned on, turned off or reversed.

The probes and probe material must be correlated with the fluid system and component being monitored. This can be readily done with little experimentation by one skilled in the art in view of this disclosure. The probe materials described above (1) can be used for monitoring corrosive reactions in hydrocarbon-containment vessels caused by sour components (such as S or $H_2S$) salt water (also sea water) or oxygen; (2) can be used for dissociation reactions in ammonia, ammonium nitrate and other chemical systems; (3) for high temperature corrosion or reactions of hydrogen sulfide, ethylene, dehydrogenation, and other chemical reaction, or (4) monitoring concentration, reaction or corrosion in acidic systems including $HCl$, $H_2SO_4$, $H_2S$, and other simple or mixed acids.

A preferred pumping means comprises an electronic pumping system which will be referred to herein as a getter-ion pump which includes getter, evaporation and sublimation type pumping action. The principal pumping action is an electronic gettering action in which free gas components are trapped in a magnetic field, ionized and accelerated by a high electrical potential into an electrode where the particle is buried in the electrode, thus removing it from the evacuated cavity. This electronic pumping action does not work well with inert gases such as helium or heavy hydrocarbon gases such as methane. Therefore, these gases which poison the electronic pumping system should be avoided. Again, these poison gases must be maintained at less than 2% of the free gas pumped for practical operation. If these poisons are present chemical gettering agents or additional specialized scrubbing equipment should be used for practical operation of the simple, efficient monitoring system of this invention.

As shown in FIG. 1, a gas detection and monitoring apparatus 10 consists of measuring apparatus 12 and control apparatus 14. The monitoring apparatus 10 is depicted as being affixed to or projected into a vessel 16 containing a body fluid 18. Fluid as defined in this specification, includes any gas, liquid, or combination thereof. Such liquids may be present in various containers such as pipelines, reactors, and other vessels, both open and closed, and may be useful in both industry and the laboratory. Thus, it should be understood that the present invention finds particular application not only in the detection and/or measurement of any preselected gas in a gas or fluid system but also in large-scale industrial corrosion inhibition applications.

The measuring apparatus 12 consists of an evacuatable probe 20 of variable geometry which can be sealingly inserted through a wall of vessel 16 to extend its inner end 22 into contact with the fluid 18. Probe 20 is formed to define a suitable evacuatable cavity 24 and the end 22 is formed to expose a gas separating plate or gas-diffusing diaphragm 26 to the fluid 18. The diaphragm 26 is sealingly connected about the end 22 of probe 20 and it may be formed of various metallic substances which allow diffusion of gas in contact with fluid 18.

While the exact nature of gas diffusion through certain metals and plastic materials is not known, the existence of the phenomena is quite well-known and is often utilized in various chemical and metallurgical processes. Thus, the diaphragm 26 may be formed from a material which is selected in accordance with its permeability to the gas present in the particular fluid system undergoing test or surveillance. Corrosion monitoring applications may require a metal or metal alloy diaphragm; in addition, a diaphragm formed of metal sheet or foil similar to that of the vessel enables increased uniformity in corrosion monitoring. Still other applications may utilize certain gas-permeable plastics and plastic-coated metallic diaphragms. Also, for the case where fluid 18 contains gas-phase hydrogen, a palladium diaphragm provides a suitable gas-diffusing member. When the ammonia molecule disassociates, for example, into $N_2$ and $3H_2$, the free $H_2$ given off can be monitored by this apparatus and the $H_2$ measured by the apparatus would be an indication of the increase or decrease in the number of ammonia molecules which are becoming disassociated. In this system, a mild steel diaphragm 26 would be satisfactory.

The probe member 20 may be formed to have an extension 28 which is attached to a stop valve 30. Valve 30 interconnects by a conduit 32 to a roughing pump 34 which may be a conventional form of vacuum pump capable of taking the pressure within cavity 24 down to a relatively low level as will be described. A vacuum level sensor 36 may be utilized in certain applications to continuously monitor the vacuum system. Vacuum level sensor 36 extends electrical connections 38 and 40 to the roughing pump 34 and valve 30, respectively, and, in the event that excessive hydrogen or other such gas is accumulated after a period of inoperation, vacuum sensor 36 serves to actuate roughing pump 34 and valve 30 to dump the accumulated gas so that the system will once again operate within the getter-ion pump range.

The opposite end of probe member 20 is formed with a connecting surface such as flange 42 which serves for connection to a getter-ion pump 44. The getter-ion pump 44 is shown as having an extension 46 and mating flange 48 which may be secured to flange 42 by suitable fasteners 50. It should be understood that the getter-ion pump 44 may take any of various designs and that the connecting portion, e.g., flanges 42, 48 and so forth, may take similarly variable forms. There are numerous, commercially available types of getter-ion pumps which may be employed.

Figure 2:
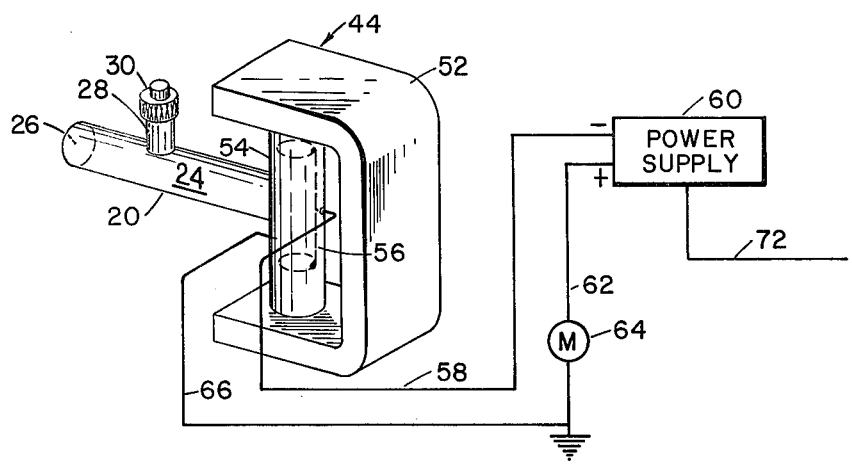
FIG. 2 is a functional diagram of one form of getter-ion pump and associated apparatus as employed in accordance with the invention.

The getter-ion pump 44 of FIG. 2 may consist of a magnet 52 bridging a cylindrically shaped collector chamber 54. The collector chamber 54 is connected coextensively with probe 20 to receive gas diffused from fluid medium 18 through diaphragm 26 and cavity 24. A collector grid 56 is supported within collector chamber 54 and grid 56 is energized by a high negative potential, e.g., 8000 volts d-c, as applied via lead 58 from a conventional form of power supply 60. A positive lead 62 is connected through a meter 64 to ground and the collector chamber 54 is grounded by means of a lead 66. Thus, detected ion current will appear as current differential exceeding a predetermined background value as read by meter 64 between ground and the positive terminal of power supply 60.

An output may also be derived from the power supply 60 by means of an electrical output lead 72, and this may be conducted to a selector 74 which may then route the output for various functions. Selector 74 may connect the getter-ion pump output via lines 76 and 78 to any one or all of a recorder 80, an alarm device 82, telemetering apparatus 84, or liquid control apparatus 86. The recorder 80 may be a conventional form of recording mechanism responsive to electrical current to provide a permanent, timeanalog indication or such, and alarm device 82 may be any of many well-known types of mechanism for alerting corrective measures or overseeing personnel. The telemetry apparatus 84 may be similarly utilized for initiating safeguard measures which are actuable from a remote position. The liquid control apparatus 86 constitutes a feedback type of control which may function to inject corrosion inhibiting substance or to apply gas phase control measures to the fluid system. The liquid control apparatus 86 finds especial value in the protection of pipelines and such vessels containing moving fluids as will be further described below.

In operation, the measuring apparatus 12 is appropriately connected to the control apparatus 14 and the probe member 20 is suitably placed in vessel 16 having fluid 18 contained therein. Probe member 20 may be sealingly connected through or inserted into vessel 16 to expose the gas-diffusing diaphragm 26 in contact with the contained fluid 18. In the case of corrosion monitoring, the diaphragm 26 may be formed of the same substance as vessel 16 to provide a known corrosion reference and uniformity with respect to corrosion effects per time. However, the diaphragm 26 may be formed of various other metals, alloys and compound structures, including plastics and rubber, as long as it is gas permeable in the enviroment of fluid 18; if the corrosivity is known or can be determined, it may be applied in reference manner to evaluate other characteristics of the vessel-fluid system.

The roughing pump 34 may then be operated through valve 20 to evacuate the gas from within cavity 24. Roughing pump 34 serves to reduce the pressure in cavity 24 to a residual on the order of $10^{-3}$ Torr which, for example, is a pressure which is low enough to assure good getter-ion pump operation. Once a suitable low pressure has been attained within cavity 24, the roughing pump 34 can be shut off and valve 30 closed such that measuring apparatus 12 will function with getter-ion pump 44 providing an output indicative of gas diffusion.

The getter-ion pump 44 functions conventionally to provide an ion current or electrical current output through power supply 60 on lead 72 in direct proportion to the amount of hydrogen or other gas which is introduced through migration along cavity 24. Referring to FIG. 2, the gas diffuses through diaphragm 26 and then migrates within cavity 24 and into the relatively high electric and magnetic fields within the collection chamber 54. The respective gas atoms or molecules are then ionized within the collection chamber 54 and attracted to the collector grid 56, which is energized at a high negative potential. The collection of charged particles is then indicated by relative values as read from current meter 64. Thus, the current produced is a direct index of the gas flow and the output or lead 72, on the order of microamperes, may be applied through selector 74 for recording, transmission, or whatever.

In corrosion applications, the current that flows from the getter-ion pump 44, as present on output lead 72, is proportional to the amount of hydrogen migrating through cavity 24 into getter-ion pump 44, and it is further proportional to the corrosion rate of the metallic vessel 16 in the environment of a corrosive-type fluid 18. Hence, the current on lead 72 can be equated to the instantaneous corrosion rate of vessel 16, and it may be applied to the recorder 80 to maintain a continuous record of corrosive activity within the metal-corrosive fluid system. Also, depending upon the type of installation, the selector 74 may be employed to route the ion current to alarm device 82, telemetry apparatus 84 or the liquid control apparatus 86. Liquid control apparatus 86 will serve to provide active control of corrosive activity as will be further described below.

Figure 3:
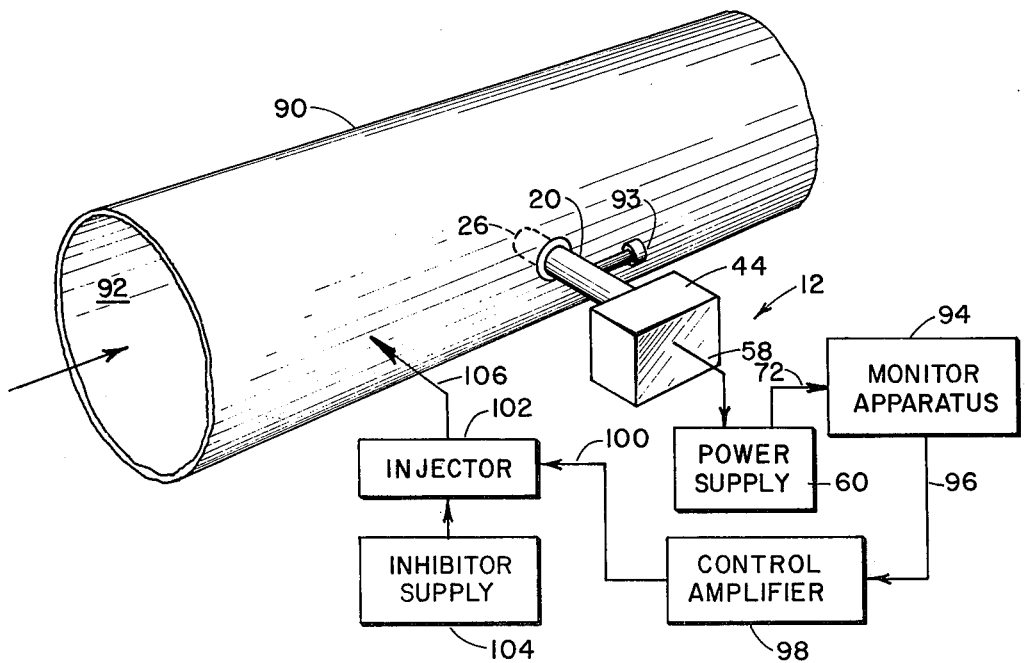
FIG. 3 is a pictorial block diagram of an exemplary usage of the invention.

FIG. 3 depicts a specialized usage of the present invention as it is applied to control or monitor corrosion in pipelines. In the operation of pipelines, it is the present practice to flow chemical inhibitors into the pipeline to guard against internal corrosion, this is particularly true with respect to sour crude pipelines and certain produce pipelines. The present invention provides a method whereby corrosivity is continually and accurately monitored to control or, rather, to match the corrosion inhibitor concentration with the degree of corrosivity in the line. Such corrosion monitoring and control alleviates the costly wastage of inhibitor which results when the liquid system is such that it would be non-corrosive anyway and, correspondingly, it protects against corrosion and related damages to the pipeline in the event that too small an inhibitor concentration were instilled.

Thus, referring particularly to FIG. 3, a metallic pipeline 90 carrying a corrosive fluid 92 under pressure can employ the measuring apparatus 12 for hydrogen detection to control the injection of corrosion inhibitor in direct proportion to the degree of corrosivity. The probe member 20 is inserted in sealed fashion through the pipeline 90 such that the hydrogen-diffusing diaphragm 26 is exposed to the corrosive environment of fluid 92. A getter-ion pump 44 is then connected to receive hydrogen diffusing through the probe member 20 to generate an ion current electrical output from power supply 60 on lead 72. A sealable stem 93 provides evacuation access for pumping air out of probe member 20. This evacuation may be effected at extended intervals with only periodic checking of condition.

The electrical output on lead 72 is then conducted to monitor apparatus 94 which may include any combination of recorders, alarms, or transmitters as shown in control apparatus 14 of FIG. 1. In addition, an electrical signal indicative of ion current is conducted on a lead 96 for input to control amplifier 98, e.g., a conventional form of differential amplifier or such. Control amplifier 98 then generates a control signal for application on lead 100 to injector 102. The injector 102 may be a solenoid operated valve or such which regulates the flow of corrosion inhibitor from an inhibitor supply reservoir 104 into pipeline 90 via an input conduit shown generally as arrow 106.

Various types of corrosion inhibitors may be contained in the inhibitor supply 104. For example, and in the case of sour crude transmission, a commercially available $H_2S$ corrosion inhibitor which may be employed would be Dualtreat 476 obtainable from United Chemical Corporation of New Mexico in Hobbs, New Mexico. Many other commercial corrosion inhibitors for use with various metalcorrosive fluid systems may be employed for injection in the circulating or moving fluid systems.

In operation, the pipeline corrosion protection system of FIG. 2 prevents economic loss through waste of corrosion inhibitor by accurately regulating the input of corrosion inhibitor to the metal-corrosive fluid system in accordance with the actual corrosive activity at that point in the pipeline. Thus, the hydrogen-diffusing diaphragm 26 experiences varying degree of corrosion in the environment of fluid 92 and this, in turn, causes proportionately varying amounts of hydrogen to diffuse through diaphragm 26 for introduction into the cavity 24 (FIG. 1) within probe member 20. Cavity 24 having been reduced to an operating vacuum level by the roughing pump 34, the getter-ion pump 44 operates to remove further produced hydrogen gas and this operation produces an ion current which is directly related in time-analog comparison to the hydrogen flow. This current is then represented as an electrical signal or electrical current flow on lead 72 to the monitor apparatus 94. Thus, the current flow on lead 72 is indicative of a vacuum loss behavior of cavity 24 which is a direct indication of hydrogen presence and removal through getter-ion pump 44.

The ion current or corrosion activity signal is conducted on lead 96 to a control amplifier 98 which provides a variable control signal on lead 100 to the inhibitor injector 102. The injector 102 then serves to vary the input of corrosion inhibitor from inhibitor supply 104 through input 106 to pipeline 90 in direct relationship to the degree of corrosivity at that time. Such variable control of the costly corrosion inhibitor substances results in a great saving in both the cost of inhibitor substances as well as the cost of pipeline repair and pipe replacement. As a further index of the utility of this apparatus, it is possible to use the mixtures of the corrosivities of various fluids to indicate the passage of various product batches in the pipeline.

Figure 4A:
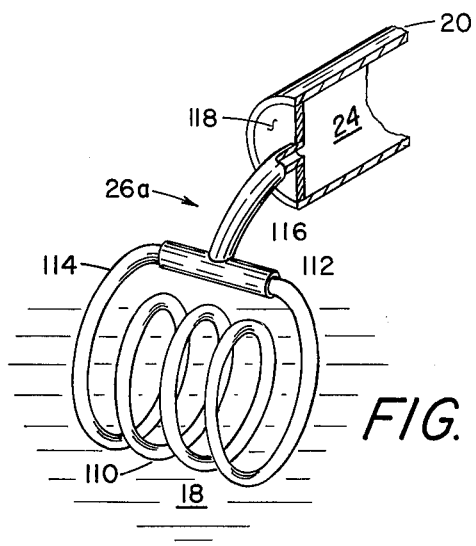
FIGS. 4A, 4B and 4C depict several alternative forms which the diaphragm may take.
Figure 4B:
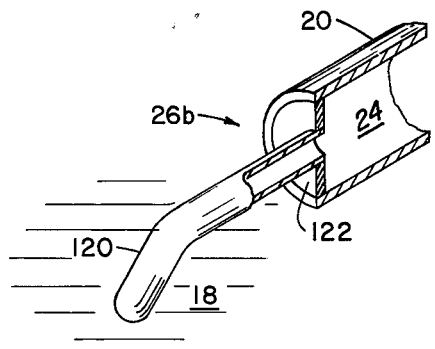
Figure 4C:
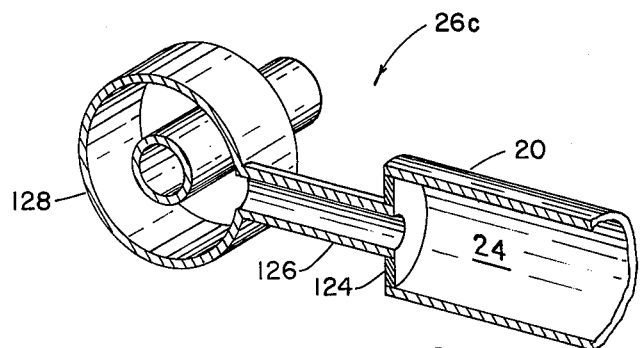

FIGS. 4A, 4B and 4C show some alternative forms which the diaphragm member 26 may take. Thus, FIG. 4A shows a diaphragm 26a which may be employed to place a greatly multiplied surface area in contact with the fluid, liquid or gas material. Diaphragm 26a consists of a hollow coil 110 of selected diaphragm material which is connected at each end through air-tight, insulative fittings 112 and 114 to a T-connector portion 116. The insulative fittings 112 and 114 prevent electrochemical action in the event that dissimilar metals are employed in contact with the fluid 18. The T-connector portion 116 is then formed with a flanged end wall 118 which is sealingly connected across end of probe member 20.

Figure 5:
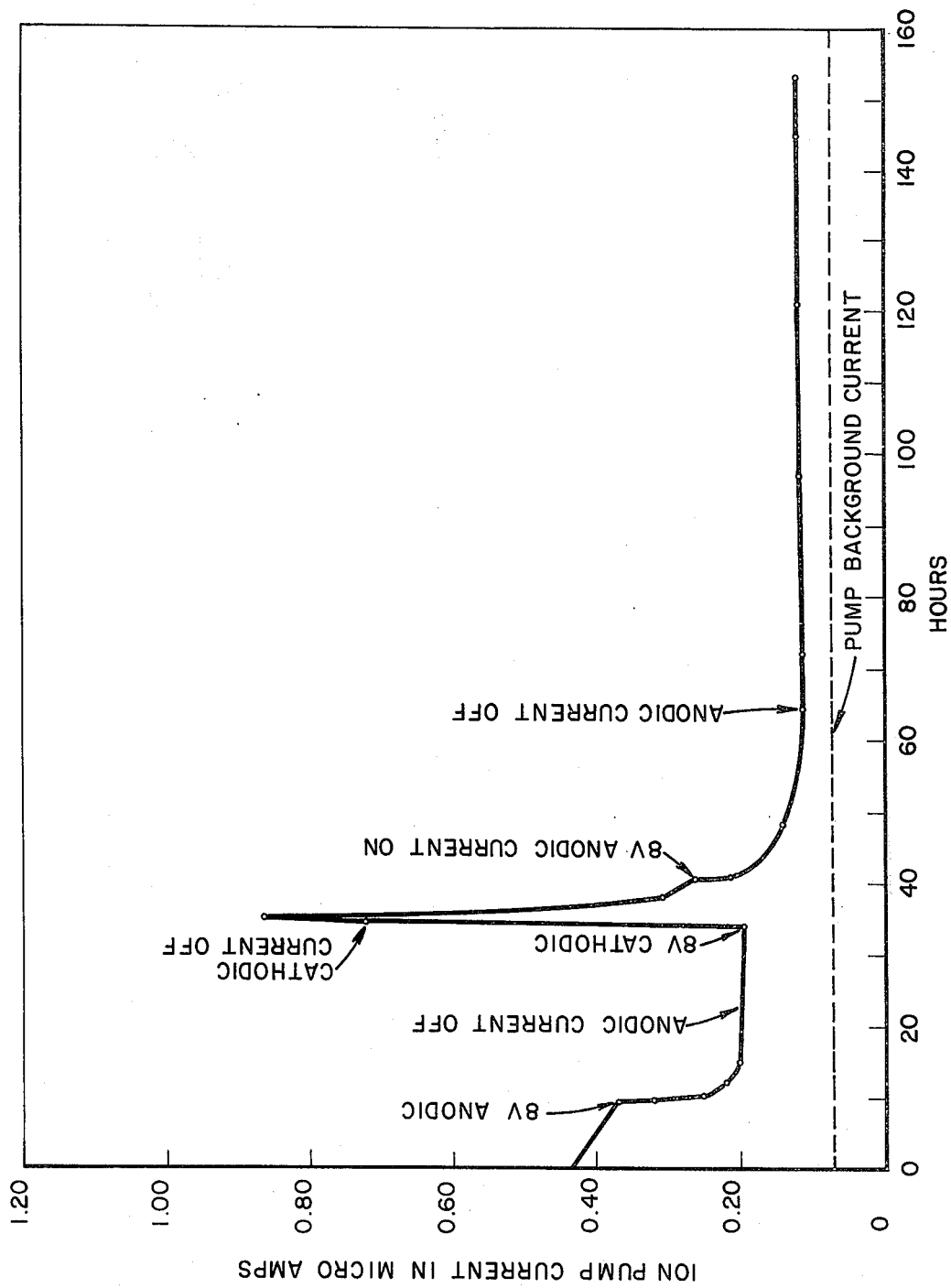
FIG. 5 is a graph illustrating ion pump current vs. hydrogen permeation over a period of time in a liquid ammonia system where anodic and cathodic potential are selectively applied during the time period.

FIG. 4B discloses another diaphragm 26b which is finger-like in character. Diaphragm 26b may be formed as an extended, closed tubular portion 120 which is flanged out into a sealing end wall 112 which can be received within probe member 20. Diaphragm 26b is intended for use in applicataions which may be adequately sampled from small area probes and/or high pressures. As shown in FIG. 4C, still another form of diaphragm 26c may find specialized application. Diaphragm 26c consists of an end wall 124, tube portion 126, and generally cylindrical sleeve portion 128 and it may find use in various other pipe protection and corrosion monitoring applications. An example of anodic curtailment of hydrogen permeation in liquid ammonia confined in an iron container is illustrated in FIG. 5. A 1-liter/sec. stainless steel magnetic ion pump was connected to a ¼ inch diameter, 12 inches long, .025 inch wall mild steel tubing. One end was sealed and inserted into the ammonia through the stainless steel container and acted as a probe. After 10 hours anodic potential of 8 volts was applied between the probe and the container. After 20 hours and anodic potential was disconnected. At 35 hours 8 volts of cathodic current was applied. It should be noted here that a drastic increase in hydrogen penetrated the stainless steel probe and was indicated by the ion pump as a large increase in current (approximately $0.90\mu$ amps.). At 40 hours the anodic potential was again supplied and the ion pump current again indicated a decrease in hydrogen permeation.

While a specific use has been set forth, it should be understood that the present invention can be employed in any fluid system wherein a gas is to be selectively examined, measured or monitored, including various corrosion control applications. It is also contemplated that the corrosion control system can be utilized to provide rapid analytical checking of circulating acid systems, such as sulfuric acid cooler lines where both random and periodic variations of acid strengths are encountered. The use of this novel analytical instrument will permit a continuous check upon the acid strength to guard against the unexpected bursts or pulses of increased corrosive activity, e.g., where random $SO_3$ concentrations form small amounts of oleum in the circulating acid line. Also, the system will find use as an analytical device in the chemical laboratory to analyze for arsenic, antimony, bismuth, and/or sulfur in certain acid systems. One practice would be to convert the acid system under inspection to its corresponding hydride system with reference pH levels, this via electrochemistry. Then the analytical instrument can be employed to measure the hydrogen input capability of the liquids to determine the particular hydrides or variations of such.

The foregoing discloses a novel gas detection and analytical system which becomes a relatively basic tool and may find many uses in various petroleum refining processes, petrochemical manufacturing operations, metallurgical process controls, laboratory research, etc. The apparatus operates on the concept whereby hydrogen or other gas is diffused through a thin (generally metallic) membrane or diaphragm which is suited to its environment for getter-ion pumping, the vacuum loss behavior due to such gas diffusion becomes the input characteristic, and it is directly readable as the ion current output of the getter-ion pump. The invention is susceptible of being employed in an automatic fashion such that it can be installed in the field and left unattended. The operating characteristics may be altered so that the apparatus can be employed with any of various metal-corrosive fluid systems at any of diverse pressure and temperature combinations.

Changes may be made in the combination and arrangement of elements as heretofore set forth in the specification and shown in the drawings; it being understood that changes may be made in the embodiments disclosed without departing from the spirit and scope of the invention.

What is claimed is:

1. An apparatus for continuous instantaneous monitoring of a selected component in a fluid system comprising gas, liquid, gas and liquid, liquid and solid, or a mixture thereof; said apparatus comprising a probe means connected to a pumping means; said probe means being removeably insertable into said fluid system and having a body portion and a diaphragm portion which will allow diffusion of said selected component defining a closed cavity which is evacuated and which connects to and communicates with said pumping means; said pumping means having an electrical molecule pumping means and a current indicating means which electronically removes molecules from said cavity, maintains evacuation of said cavity and indicates the molecule pumping rate as electrical current; said electrical molecule pumping means having at least two electrodes in a magnetic field with an electrical potential between said electrodes with one electrode being an anode and one electrode being a cathode so that molecules in said cavity pass into said magnetic field, are accelerated into an electrode and indicated as an electrical current; said probe having a geometry and size so that the probe can be sealably installed through a port in a vessel wall with the diaphragm portion of said probe exposed to said fluid system with the diaphragm portion of said probe being of such size, material, and configuration to allow selective diffusion of said selected component at a controlled rate; said current being transmitted to a receiving means as a signal and being indicated, recorded, or a combination thereof as a current magnitude; said signal being transmitted to a controlling means with an injector means which injects a composition into said fluid system to effect the selected component being monitored.

2. An apparatus of claim 1 wherein the probe, detecting means, receiving means, controlling means, and injector means maintain a selected component at a value in a preselected range by matching the injected composition with that required to control the component being monitored.

3. An apparatus of claim 2 wherein the selected component being monitored is an ion which is detected and derived from hydrogen, nitrogen, ammonia, air, hydrogen sulfide, and mixtures thereof.

4. The apparatus of claim 1 wherein the diaphragm portion of said probe means is formed of hydrogen-diffusing material, said fluid system is contained in a pipeline, and said composition is a corrosion inhibitor.

5. The apparatus of claim 4 wherein said fluid system is crude oil containing hydrogen sulfide.

* * * * *